United States Patent [19]
Oh et al.

[11] Patent Number: 5,863,742
[45] Date of Patent: Jan. 26, 1999

[54] INHIBITION OF PROTEASE ACTIVITY OF HUMAN WHOLE BLOOD CELL LYSATES

[75] Inventors: Se-Kyung Oh, Brookline, Mass.; Harry Towbin, Allschwil, Switzerland

[73] Assignee: Chiron Diagnostics Corporation, Walpole, Mass.

[21] Appl. No.: 212,442

[22] Filed: Mar. 10, 1994

[51] Int. Cl.$^6$ .................................................. G01N 33/567
[52] U.S. Cl. ...................... 435/7.21; 435/79; 435/7.92; 435/7.94; 435/962; 435/967; 435/70.21; 435/240.27; 435/22; 435/23; 435/24; 435/183; 435/184; 435/219
[58] Field of Search ..................................... 435/7.21, 7.9, 435/7.92, 7.94, 962, 967, 70.21, 240.27, 22, 23, 24, 183, 184, 219

[56] References Cited

U.S. PATENT DOCUMENTS

| | | | |
|---|---|---|---|
| 4,554,088 | 11/1985 | Whitehead et al. | . |
| 4,727,036 | 2/1988 | Knowles et al. | 436/547 |
| 5,114,844 | 5/1992 | Cohen et al. | 435/7.21 |
| 5,198,350 | 3/1993 | Horisberger et al. | . |
| 5,242,802 | 9/1993 | Berger | 435/7.9 |
| 5,252,459 | 10/1993 | Tarcha et al. | . |

FOREIGN PATENT DOCUMENTS 0 360088A3  8/1989  European Pat. Off. .

OTHER PUBLICATIONS

Dreiding, et al., (1985) Virology 140: 192–196.
Ezekowitz, et. al., (1992) New England Journal of Medicine 326: (22) 1456–1463.
Goren, et al., (1983) Virology 130: 273–280.
Hartshorn, et al., (1987) Antimicrobial Agents and Chemotherapy 31: (2) 168–172.
Hochkeppel, et al., (1992) Drugs of the Future 17: (10) 899–914.
Horisberger, (1992) Journal of Virology 66: (8) 4705–4709.
Horisberger, et al., (1987) Journal of Interferon Research 7: 331–343.
Horisberger, et al., (1983) Proc. Natl. Acad Sci. USA 80: 1910–1914.
Horisberger, et al., (1988) Somatic Cell and Molecular Genetics 14: (2) 123–131.
Jakschies, et al., (1990) Journal of Biological Response Modifiers 9: (3) 305–312.
Laemmli, (1970) Nature 227: 680–685.
Manwaring, (1906) Tr. Chicago Path Soc. 6: 425–427.
Melen, et al., (1992) The Journal of Biological Chemistry 267:(36) 25898–25907.
Meurs, et al., (1990) Cell 62: 379–390.
Revel, et al., (1986) TIBS II: 166–170.
Ronni, et al., (1993) Jouranl of Immunology 150: (5) 1–12.
Sen, et al., (1992) The Journal of Biological Chemistry 267: (8) 5017–5020.
Simon, et al., (1991) Journal of Virology 65: (2) 968–971.
Staeheli, et al., (1985) Molecular and Cellular Biology 5: (8) 2150–2153.
Towbin, et al., (1992) Journal of Interferon Research 12: 67–74.
von Wussow, et al., (1989) Arthritis and Rheumatism 32: (7) 914–918.
von Wussow, et al., (1990) Eur. J. Im. 20: (9) 2015–9.
Weber, et al., (1969) J. Biol. Chem. 244: 4406–4412.
T.E. Creighton, ed. Protein Function: A Practical Approach, New York: IRL Press, 1992, pp. 1–10.
Deutscher, M.P., ed. Guide to Protein Purification. Methods in Enzymology 182: 87–88, 1990.
Melen, K. et al. "Enzymatic Characterization of Interfron–induced Antiviral GTPases Murine Mx–1 and Human MXT Proteins." J. Biol. Chem. 21 (3) 2009–2015, 1994.

*Primary Examiner*—Paula K. Hutzell
*Assistant Examiner*—Benet Prickril
*Attorney, Agent, or Firm*—Arthur S. Morgenstern; Robert P. Blackburn

[57] ABSTRACT

A method of inhibiting proteolytic degradation of a thermally-stable intracellular protein is described. The method involves adding 1 or more denaturing agents to a sample which contains the protease and the protein of interest and heating the resulting solution at a temperature and for period of time sufficient to denature the protease. The method optionally includes a step for lysing the cell if the protein of interest is contained in a cell in order to release said protein. Additionally, a method of determining Mx protein induced by interferon in a blood sample is described. The method involves adding to a blood sample a lysing agent, a denaturing agent, and a detergent selected to solubilize Mx protein. The sample containing Mx protein is then heated at a temperature of from about 50° C. to about 60° C. for a period of time of from about 1 minute to about 30 minutes, and the Mx protein in the solution then is determined. Also described is a solution including a synthetic matrix mimicking whole blood cell lysates, or actual whole blood cell lysates, to which a known concentration of a thermally-stable intracellular protein is added to prepare a control material. In addition, a solution free of a protease that degrades the intracellular protein is disclosed, such solution remaining stable at 4° C. for at least three weeks.

1 Claim, 5 Drawing Sheets

INHIBITION OF PROTEASE ACTIVITY OF HUMAN WHOLE BLOOD CELL LYSATES

FIELD OF THE INVENTION

The present invention relates generally to inhibition of protease activity in biological fluids, and more specifically to a method of inhibiting proteolytic degradation of Mx protein in human whole blood cell lysates, and employing an Mx protein assay as the method that is indicative of the efficacy of interferon therapy.

BACKGROUND OF THE INVENTION

Proteolytic degradation is a naturally occurring process in all biological kingdoms. Proteolytic degradation also complicates scientific investigation if one wants to examine the undegraded level of proteins. Determination of intracellular protein or membrane proteins is particularly complicated by proteolytic degradation, as the cell lysing process also releases proteases. A variety of protease inhibitors exist for inhibition of proteolytic degradation, and such conventional inhibitors are known to those of ordinary skill in the art. However, when the effectiveness of known protease inhibitors is not sufficient to halt the proteolytic degradation of a protein of interest, or addition of these inhibitors only accelerated proteolytic degradation, one would have to find an alternative way to arrest this problem.

An example of the type of investigation that is complicated by proteolytic degradation is the accurate determination of protein in biological fluid. Such protein determination may also be useful to assess the clinical relevance of therapy via determination of the protein specifically induced by the species of interest.

For example, it is important to evaluate the clinical efficacy of interferon therapy, which is both costly and increasingly popular in the treatment of such conditions as hemangiomas in children, genetically predisposed multiple sclerosis, autoimmune diseases, certain types of cancer, and AIDS. Assaying the circulating level of interferon is technically difficult. However, by assaying an intracellular protein called Mx protein induced specifically by interferon, the efficacy of interferon therapy may be assessed. In a paper entitled, "A Whole Blood Immunoassay for the Interferon-Inducible Human Mx Protein", by Towbin, et al., Journal of Interferon Research, 12, 67 (1992), the authors describe an assay procedure for Mx protein in whole blood cell lysates using an enzyme immunoassay.

Although strides in interferon research in general and Mx protein investigation in particular have been made, it remains a goal to determine the uncompromised level of Mx protein by minimizing proteolytic degradation of Mx protein in evaluating the new application of interferon therapy.

Accordingly, it is an object of the present invention to provide a method of inhibiting proteolytic degradation of an intracellular protein, i.e., Mx protein in cell lysates. It is still another object of the invention to provide an artificial matrix solution whereby an intracellular protein can be kept stable against proteolytic degradation at a temperature at or below 4° C. for at least three weeks.

SUMMARY OF THE INVENTION

The foregoing and other objects and advantages of the invention are achieved by providing a method of inhibiting proteolytic degradation of a thermally-stable intracellular protein in cell lysates. The method involves forming a solution containing one or more denaturing agents and unknown proteases that degrade the intracellular protein, and heating the solution at a temperature and for a period of time sufficient to denature the protease.

The solution may be defined as detergent lysed whole blood cells. The solution may be defined in part by a synthetic matrix mimicking blood cell lysates as well. When the solution contains the intracellular protein such as in whole blood lysates, the heating step is carried out at conditions which do not destroy it. When the solution is free of intracellular protein, such as in a synthetic matrix simulating cell lysates, harsher conditions may be applied until all of the protease activity is destroyed.

The present invention also provides an indirect method of determining interferon in patient blood. The method involves heating a sample in the presence of denaturing agents, in order to denature 1 or more unknown proteases from cell lysates that degrade the intracellular protein of interest, e.g., Mx protein. Heat is applied at a level and for a period of time sufficient to denature the proteases, but not to denature the intracellular protein. The intracellular protein is then determined.

Determination may be made by way of an assay, in a manner to detect the presence of the protein induced by interferon, thus indirectly determining the biological effectiveness of the interferon therapy. Such an assay may involve the steps of providing a binding partner of the intracellular protein to a solid phase capture antibody, allowing the binding partner to capture the intracellular protein by contacting the solid phase with the solution, and coupling a second binding partner of the intracellular protein to the intracellular protein. The second binding partner carries a chemiluminescent label, which may be detected by a luminometer. The coupling steps may be combined in any order.

The present invention also provides an artificial matrix which is made to be protease-free. Intracellular Mx protein remains stable in this artificial protein solution at a temperature of 4° C. for at least three weeks. According to one aspect of the invention, the solution includes whole blood cell lysates. According to another aspect, the solution includes a synthetic matrix mimicking whole blood cell lysates.

Other advantages, novel features and objects of the invention will become apparent from the following detailed description of the invention, in conjunction with the accompanying figures.

DETAILED DESCRIPTION OF THE PREFERRED EMBODIMENT

The present invention provides a method of inhibiting proteolytic degradation of a thermally-stable intracellular protein by treating cell lysates with heat and 1 or more denaturing agents at a temperature and for a period of time sufficient to denature the protease. As protease activity is inhibited according to the method of the invention, an assay to determine the presence and/or concentration of the intracellular protein may be reliably performed. Provision of an assay sample that is stable against proteolytic degradation is advantageous when the sample must be stored for any period of time prior to performance of the assay. Additionally, an artificial mixture of protein solution stable against proteolytic degradation of the protein of interest may be provided and used as a diluent for an antigen standard, controls, calibrators, or the like.

Inhibition of the proteolytic degradation of any of a wide variety of thermally stable proteins is provided in accordance with the invention. As used herein, the term "thermally-stable" is meant to define the stability of the protein of interest at a temperature and for a period of time necessary to degrade the protease responsible for degradation of the protein. Thermally-stable proteins include, but are not limited to, some membrane proteins (e.g., carcinoembryonic antigen) and intracellular proteins, which include nuclear proteins (e.g., murine Mx protein) and cytoplasmic proteins (e.g., human Mx protein, heat-shock proteins and cytoskeletal proteins).

According to one aspect of the invention, a method of inhibiting proteolytic degradation of an intracellular protein (e.g., Mx protein) induced by interferon is provided. Such a method makes feasible the reliable, reproducible determination of Mx protein, thus determining the clinical efficacy of interferon therapy. Approximately 30 different proteins are known to be induced by interferon. However, only 2,5-oligo-(A)' synthetase, p68 kinase, and Mx protein are known to mediate anti-viral actions of interferon, and determination of one or more of these proteins in accordance with the invention is thus highly relevant to evaluation of interferon therapy.

Determination of Mx protein is particularly preferred for the following reasons: Mx is promptly induced (2 hrs.) after interferon treatment, and reaches maximum levels in a relatively short period of time (approximately 36 hours). Cellular induction of Mx protein is not subject to feedback inhibition even at high doses of interferon therapy. Additionally, the biological half-life of Mx protein is relatively long ($T_{1/2}$ is 3.5–5 days). Thus 20–30% of the initial Mx protein level remains even at 2 weeks following the cessation of interferon therapy. Thus, due to its long half-life, Mx protein is a good indicator of interferon effectiveness. Furthermore, the fact that it is easily detectable makes it a rapidly inducible, sensitive and reliable indicator of interferon action in a wide range of interferon doses.

According to the method of the invention, a solution containing a denaturing salt, detergents, and proteases that degrade(s) the intracellular protein is heated at a temperature and for a period of time sufficient to denature the protease. The solution may be formed by lysing cells, for example human whole blood cells or cultured cells.

The solution also may be formed by creating an artificial matrix that mimics blood. Many artificial matrices mimicking whole blood are suitable for use in accordance with the present invention. Preferably, an artificial matrix formulated in accordance with the present invention and composed of protease-free bovine serum albumin and crystalline bovine hemoglobin is employed.

A wide variety of denaturing agents are known to those of ordinary skill in the art, and may be used according to the method of the invention, including a but not limited to a urea and guanidine hydrochloride, which are preferred denaturing agents. Proteases to be inhibited in accordance with the present invention include virtually all those known to exist in white blood cells, including Cathepsin G, elastase, metalloproteases, etc.

When the method of the invention has been carried out, that is, when a solution has been treated so as to denature a protease that degrades an intracellular protein, that solution then may be spiked with the intracellular protein without risk of proteolytic degradation. Such a solution may serve as a diluent for an antigen standard in an assay, and may contain whole blood cell lysates, or a synthetic matrix mimicking whole blood cell lysates. According to a preferred embodiment of the present invention, such a solution remains stable at a temperature of 4° C. for at least 3 weeks.

According to another embodiment, the solution may serve as a standard in an assay, or may comprise a sample in an assay, for example, a human whole blood sample. When the solution contains whole blood cells or cultured cells, a lysing agent is advantageously included in the solution prior to heating the solution in the presence of the denaturing agents. Thus, cells may be lysed and the protease denatured in a single step.

A variety of lysing agents are suitable for use in accordance with the present invention, including but not limited to non-ionic detergents such as monodisperse and polydisperse, homogeneous and heterogeneous polyoxyethylenes. Preferred lysing agents include Tergitol NP-40 a trademark of Union Carbide for nonyl Phenoxy Polyethoxy ethanol or Triton X-100 a trademark of Rohm and Hass for t-octyl phenoxy polyethoxy ethanol, which should be added in an amount such that its concentration, when the sample is heated in the presence of other denaturing agents (such as urea and guanidine hydrochloride), should be sufficient to denature the protease.

Although it is not important whether the cells are lysed before or at the same time the protein is solublized, it is important that the non-ionic detergent used to lyse the cells be included in the denaturing medium, since the non-ionic detergent aids the denaturing process. In the case where lysing is not required (e.g., when a synthetic matrix is used), the non-ionic detergent still should be added along with 1 or more other denaturants (e.g., urea or guanidine hydrochloride) and the anionic detergent (e.g., SDS) to assure that denaturation occurs. Depending on the cell involved, even other lysing agents may be appropriate. For example, in the case of red blood cells, water is sufficient for lysing the cell. However, when the cell is lysed using an agent aside from a nonionic detergent, the nonionic detergent must still be used for denaturing the protease.

Although SDS combined with heat has been used in the past to mask the charge of the native configuration of proteins, thus frequently resulting in their denaturation (see Laemmli, Nature 227:680 (1970)), the use of SDS, denaturant (e.g., urea) and heat in a controlled fashion in the instant invention results only in the destruction of proteases, without denaturing the protein of interest. The solution is heated in the presence of a denaturing agent at a temperature and for a period of time sufficient to denature the protease. The temperature and time of heating should be selected as to sufficiently denature the protease, and when the solution contains the intracellular protein, the temperature and time should be selected so as not to denature the intracellular protein. A temperature of no less than 50° C. should be selected, and the solution should be heated for at least 60 seconds. If the intracellular protein is present in the solution, the solution should be heated at a temperature of from about 50° C. to about 60° C. for a period of time of 15–30 minutes. If the solution contains only the artificial matrix (i.e., contains protease contamination but does not yet contain the protein of interest), harsher conditions may be employed before the protein of interest is added to the matrix. For example, such a solution may be heated at a temperature of from about 50° C. to about 100° C. for a period of time of from about 1 minute to 1 hour or more, preferably at a temperature of about 56° C. for about 1 hour (see Manwaring, W. H. (1906) on the destruction of complement by heat, TR. Chicago Path Soc. 6:425).

When a solution contains the intracellular protein, the solution conditions should be kept within a range compatible with survival of such a protein. Specifically, the pH of the solution should be kept within a range of 7.0–8.0, and the ionic strength of the solution should be kept at a level not more than about 4M.

As noted above, a solution in accordance with the present invention that contains a thermally-stable intracellular protein (e.g., Mx protein) and that is free of a protease that degrades the Mx protein facilitates a reliable and reproducible assay to determine the intracellular Mx protein. As used herein, the term, "determine" is meant to define detection of the intracellular protein at the limit of the assay, or determination of the concentration in solution of the intracellular protein. Many types of assays are known in the art which may be modified so as to be employed in a determination in accordance with the present invention. General assay types include, for example, direct, indirect, competitive and sandwich-type heterogeneous or homogeneous assays such as those described in U.S. Pat. No. 5,252,459, issued Oct. 12, 1993 to Tarcha et. al. and incorporated herein by reference.

When human blood is to be assayed for Mx protein in accordance with a particularly preferred embodiment of the present invention, an assay method may be carried out as follows: A solution containing the proteins derived from the whole blood cells is formed by, as described above, combining the lysing agent, 1 or more denaturing agents (preferably urea) plus sodium dodecyl sulfate (SDS), the detergent selected to denature the protease and solubilize the Mx protein. Furthermore, it is important that the protease be sufficiently dilute so that the denaturants are effective. The solution is then heated at a temperature of from about 50° C. to about 60° C. for a period of time of about 15–30 min, and Mx protein is then determined.

Variations of the present invention are possible for a variety of proteins so long as the temperature at which the proteases are destroyed is determined and found to be lower than the temperature at which the analyte is denatured. Furthermore, the proper lysing agent, generally a non-ionic detergent, and a proper solublizing/denaturing agent, generally an ionic surfactant, such as the anionic surfactant sodium dodecyl sulfate, and the denaturant salts (e.g., urea or guanidine) must be used. If the sample obtained is already lysed, there is no need to include the non-ionic (lysing) agent in the system.

Further variations of the present invention are possible. For example, the sample suspected of containing interferon may be a whole blood sample, packed blood cells, tissue cultured cells, a solution containing lysed whole blood cells, synthetic matrices to which Mx protein is added to simulate whole blood lysates or the like. Other variations will become apparent to those with ordinary skill in the art.

The following examples are intended to illustrate the benefits of the present invention, but do not exemplify the full scope of the invention. For example, although a specific denaturing agent, solubilizing detergent and lysing agent are exemplified, a variety of such agents may be employed. While the determination of Mx protein and corresponding preparation of standard and control solutions containing Mx protein are exemplified, a variety of thermally-stable proteins, including but not limited to those induced by interferon or other cytokines or other biological response modifiers, are understood to be within the scope of the present invention. These and other modifications and their equivalents are understood to be within the scope of the present invention.

EXAMPLES

Materials and Methods

The protease inhibitors phenylmethylsulfonyl fluoride (PMSF), aprotonin, antipain, chymostatin, leupeptin, pepstatin A, tosyl-lysine chloromethyl ketone (TLCK), tosyl-phenylalanine chloromethyl ketone (TPCK), epsilon-amino-caproic acid (EACA), elastinal, and E-64 were purchased from Sigma Chemical Co.(St. Louis, Mo.). A non-ionic detergent, NP-40 (used to solubilize leukocytes), 2-mercaptoethanol (2-ME), protease-free bovine serum albumin (BSA-PF), radioimmunoassay (RIA)-grade BSA (BSA-RIA) and crystalline bovine hemoglobin (bHB) were also purchased from Sigma Chemical Co. Sodium dodecyl sulfate (SDS) was purchased from BioRad Laboratories (Hercules, Calif.). Some proteases, i.e. elastases (porcine pancreas and human leukocytes), cathepsin G (human leukocytes) were also Sigma chemicals. Crystalline trypsin was obtained from Worthington Biochemicals (Freehold, N.J.), and PEFAbloc™, an analog of phenylsulfonyl fluoride, was obtained from Pentapharm AG (Basle, Switzerland). All other chemicals were reagent grade chemicals from Mallinkrodt (Paris, Ky.). DEAE Sephadex A25 and 12.5% Phast gel were obtained from Pharmacia Biotech Inc. (Piscataway, N.J.). Goat serum from Ventrex Laboratory (Portland, Me.) was heat-inactivated and filtered through 0.2 um Millipore filter prior to use. Immobilized Protein-A Affinity Pak™ was purchased from Pierce Chemicals Co. (Rockford, Ill.) and used as described by the manufacturer.

Example 1

Investigation of Proteolytic Degradation of Mx Protein

An investigation was made of degradation of Mx protein in normal human plasma (NHP), whole blood lysates (WBL), packed blood cell lysates (in the absence of plasma; BCL), in synthetic matrices mimicking whole blood lysates, and in protease-free controls.

Mx protein in cultured cell lines (i.e. WISH, CHO, 3T3) was induced with interferon (B/D) (Ciba-Geigy, Basle, Switzerland), and the cells were lysed and stored frozen at −80° C. until used. An ELISA assay demonstrated that endogenous Mx protein present in frozen cell lysates exhibited a much lower quantity of immunoreactive Mx protein after freeze-thaw than an original fresh sample. In contrast, recombinant Mx protein produced in *E. Coli*, purified to homogeneity and stored at −80° C. until used retained 100% of its initial immunoreactivity upon repeated freezing and thawing.

A known quantity of purified rMx protein was spiked into two different BSA preparations, i.e. BSA-PF (protease-free) and BSA-RIA, as well as into lysed whole blood freshly drawn from a normal healthy volunteer. Both the whole blood lysate and two different BSA preparations contained a lysing agent, specifically 2%(v/v) Tergitol NP-40 detergent as described by Towbin, et al., referenced above. These preparations were further diluted with a medium containing a denaturing agent, specifically 2M urea, and a solubilizing detergent, specifically 0.1% SDS and a buffer salt, i.e., 50 mM Tris-HCl (pH 8.0). A final protein concentration was adjusted to 1%. Mx protein was spiked into a synthetic matrix composed of BSA-PF and crystalline bHB.

These samples were incubated at 37° C. for up to 120 min. Aliquots of samples were removed periodically and the amount of Mx protein remaining in the solution was correlated with a drop in signal (RLU's) over time as determined in a chemiluminescent immunoassay.

Mx protein spiked into the BSA-PF underwent minimal degradation during this incubation period. In contrast, the BSA-RIA rapidly degraded Mx protein within the first 30 minutes and Mx protein in whole blood lysate was continuously degraded throughout a 2-hour incubation period. Mx protein spiked into a synthetic matrix composed of BSA-PF and crystalline bHB was also degraded.

Since Mx protein was minimally degraded in BSA-PF, we surmised that the crystalline bHB must have been the source of this protease activity. Indeed, synthetic matrices with increasing concentrations of hemoglobin exhibited a greater degree of proteolytic degradation of Mx. Mx protein was degraded faster in packed blood cell lysates (in the absence of plasma), than in whole blood lysates.

Figure 1:
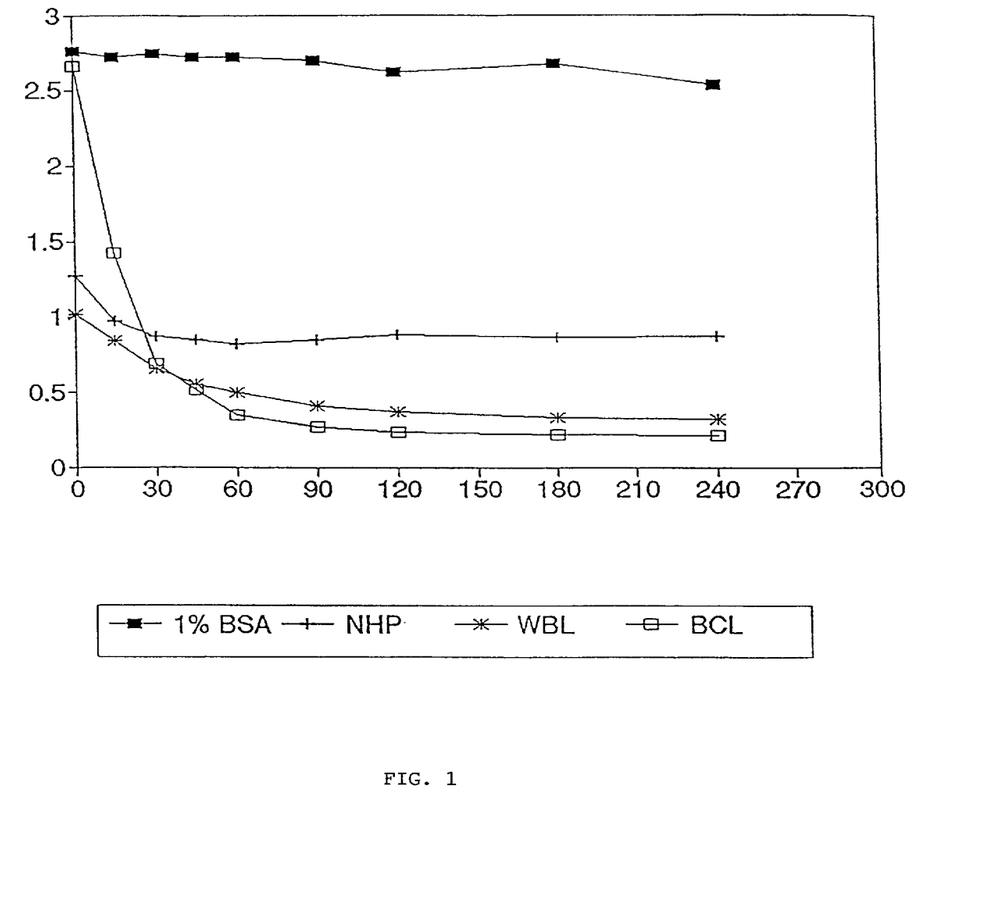
FIG. 1 is a graphic illustration of comparative degradation of Mx protein in normal human plasma, whole blood lysate, packed blood cell lysate, and in protease-free bovine serum albumin, in units of O.D. at 405 nm vs. length of incubation at 37° C. in minutes.

FIG. 1 graphically illustrates results of this assay, showing significant diminution of Mx protein in normal human plasma (NHP), whole blood lysates (WBL) and in packed blood cell lysates (BCL), compared to a control (1% BSA). It was clear from this investigation that Mx protein is subject to proteolytic degradation in a variety of biological fluids, importantly blood cell lysates. These results indicated a definite need to eliminate the protease activity in the synthetic matrices as well as in whole blood lysates before one could reliably and reproducibly determine the quantity of Mx protein in clinical samples.

Example 2

Preparation of Whole Blood Lysates

Whole blood lysates from normal healthy volunteers were prepared by adding 2% (v/v, final concentration) of NP-40 detergent to freshly drawn blood, collected in EDTA-or heparin-containing tubes and served as untreated controls. Clinical samples from clinical trials of Interferon (B/D) were also prepared in the same way as the normal control blood lysates and kept frozen at −80° C. until used.

Example 3

Formulation of synthetic matrices for Mx protein

A series of synthetic matrices which simulate the whole blood lysates of individuals with various hematocrits were formed. These synthetic matrices were composed of BSA-PF and bHB in PBS as follows:

|     | 15%   | 30.0%   | 45.0%   | 70.0%   |
| --- | ----- | ------- | ------- | ------- |
| bHB | 5 g%  | 10.0 g% | 15.0 g% | 23.0 g% |
| BSA | 7 g%  | 5.5 g%  | 4.5 g%  | 2.5 g%  |

The purpose of these synthetic matrices was to investigate the potential effects of variable hemoglobin content on the signal readout of an Mx assay and to define the most suitable hemoglobin content to formulate a synthetic matrix.

Example 4

Development of Assay for Mx Protein Determination

1. Monoclonal antibodies to Mx protein

Two separate monoclonal antibodies, one directed to the C- terminal (clone 1302.5.32) and the other to the N-terminal (clone 1302.34.16.2.44) portion of Mx protein were utilized as capture and detector antibodies in a sandwich-type immunoassay. These antibodies were purified from the mouse ascites fluids using protein-A Sepharose media and proved to be >95% pure by densito-metric scanning of the Coomassie Blue stained SDS-PAGE gel (laemmlie, ibid. Clone 1302.5.32 monoclonal antibody, directed to the C terminal of Mx protein, was conjugated to paramagnetic particles (PMP) using the glutaraldehyde activation method of Whitehead et al. as disclosed by U.S. Pat. No. 4,554,088. The PMP-conjugated antibody was suspended at 10 mg/ml in PMP wash buffer, which contained 0.25% BSA (protease-free), 0.7% bovine gamma globulin (BGG, Pentex, Miles Scientific, Naperville, Ill.), and 0.1% sodium azide in phosphate buffered saline (PBS) and used as solid-phase capture antibody. Clone 1302.34.16.2.44 monoclonal antibody, directed to the N-terminal of Mx protein, was labeled with acridinium ester using the N-hydroxysuccinimide-activated dimethyl acridinium ester (DMAE-NHS, Ciba-Corning Diagnostics Corp., Walpole, Mass.) at a molar ratio of DMAE: antibody=20: 1 at room temperature for 30 min. with constant stirring. The free DMAE and the DMAE-labeled antibody were separated by chromatography on a DEAE-Sephadex A25 column in PBS. One ml fractions were collected and the labeled antibody fractions were monitored using an MLA-I or II luminometer (Ciba-Corning Diagnostics Corp. Oberlin, Ohio). Fractions containing the DMAE-labeled antibody were pooled, diluted to a final concentration of $10^{12}$ relative luminescence units (RLU)/ml in PBS containing 1% BSA-PF, 2% Tergitol NP-40 and 0.1% sodium azide. Both antibody preparations were stored at 4° C. until used.

2. Development of a Chemiluminescent assay Purified recombinant Mx-protein (rMx) derived from the inclusion bodies of *E. Coli* (See Horisberger, et al. "cDNA Cloning and Assignment to Chromosome 21 of IFI-78-k Gene, The Human Equivalent of Murine Mx Gene", Somatic Cell & Molecular Genetics, 14, 123 (1988)) was used as an antigen standard. The protein content was determined both by a BioRad protein assay using a BSA standard and by quantitative Western blotting of a 2-D gel as described by Towbin et al. referenced above. The quantity of Mx protein was confirmed in a modified version of an ELISA assay originally published by Towbin, et al. for whole blood lysates. The modified version utilized a larger sample volume (50 ul vs. 20 ul sample) and larger amounts of primary (50 ul vs.

40 ul) and secondary antibodies (100 ul vs. 50 ul). The purified rMX protein served as the antigen standard in the modified ELISA assay. For the chemiluminescent immunoassay of Mx protein, all samples or synthetic matrices containing a known quantity of Mx protein were incubated in 12×75 mm plastic tubes simultaneously with DMAE-labeled detector antibody and PMP-conjugated capture antibody. The incubation period varied from 30 min. to 120 min. at 37° C. in a water bath. At the end of each incubation period, the solid phase-bound immune complex was separated with a magnetized separator rack, Magic Rack™ (Ciba-Corning Diagnostics Corp., E. Walpole, Mass.) for 3 min. at room temperature. The unbound antigen or antibody was discarded by decanting. The separated pellets were then resuspended in 1 ml of deionized water using a Multi-Tube Vortexer (Model 4010, Corning, N.Y.) and PMP pellets were separated, and the unbound material was removed as above. These pellets were washed once more with 1 ml of deionized water and finally resuspended in 0.1 ml of deionized water before counting in an MLA-I or -II luminometer. For the automated assays, the ACS:180™ (Ciba-Corning Diagnostics Corp. Oberlin, Ohio) was used and the data was analyzed using mathematical algorithms generated by a statistical program.

3. Preparation of detector antibody with DMAE label

Using the DMAE-labeling procedure described in the Materials and Methods section, we obtained DMAE-labeled antibody with a specific activity of $7 \times 10^{11}$ relative luminescence units (RLUs) per mg of detector antibody (clone 1302.34.16.2.44), with luminescence determined by a luminometer and protein concentration determined by a BioRad protein assay. The detector antibody was purified with the protein-A-Sepharose media as suggested by the manufacturer. The DMAE-labeled antibody reacted with the solid phase-bound Mx protein in a dose-dependent manner, similar to the biotinylated antibody used in ELISA. This result indicates that DMAE-labeling did not destroy the immunoreactivity of detector antibody to Mx antigen.

4. Preparation of PMP-bound antibody

The capture antibody (clone 1302.5.32) was conjugated to PMP at a coupling efficiency of 74%, resulting in 150 mg antibody bound per gm of PMP. The PMP-conjugated antibody reacted in a dose-dependent manner with a separate epitope of rMx, which is not occupied by DMAE-labeled antibody.

5. Development of chemiluminescent assay for Mx protein

A. Effect of the biochemical nature and total protein concentration of matrices on chemiluminescent signal output Since whole blood lysates consist mainly of hemoglobin and serum albumin, the effect of these two proteins on chemiluminescent signal output was examined. The effect of the total protein concentration of the synthetic matrix on chemiluminescent signal was also examined. Hemoglobin at the same 1 g % (w/v) concentration, exhibited only ¹⁄₁₀ of the chemiluminescent signal output compared to that of 1% BSA. On the other hand, 2 g % of total protein (1:10 dilution of goat serum +15 g % human hemoglobin) generated only ½ of the signal output generated with 1% total protein. Thus, the biochemical nature of protein, (i.e. hemoglobin vs. BSA) as well as the concentration of total protein both influence the signal output of the chemiluminescent assay.

Figure 2:
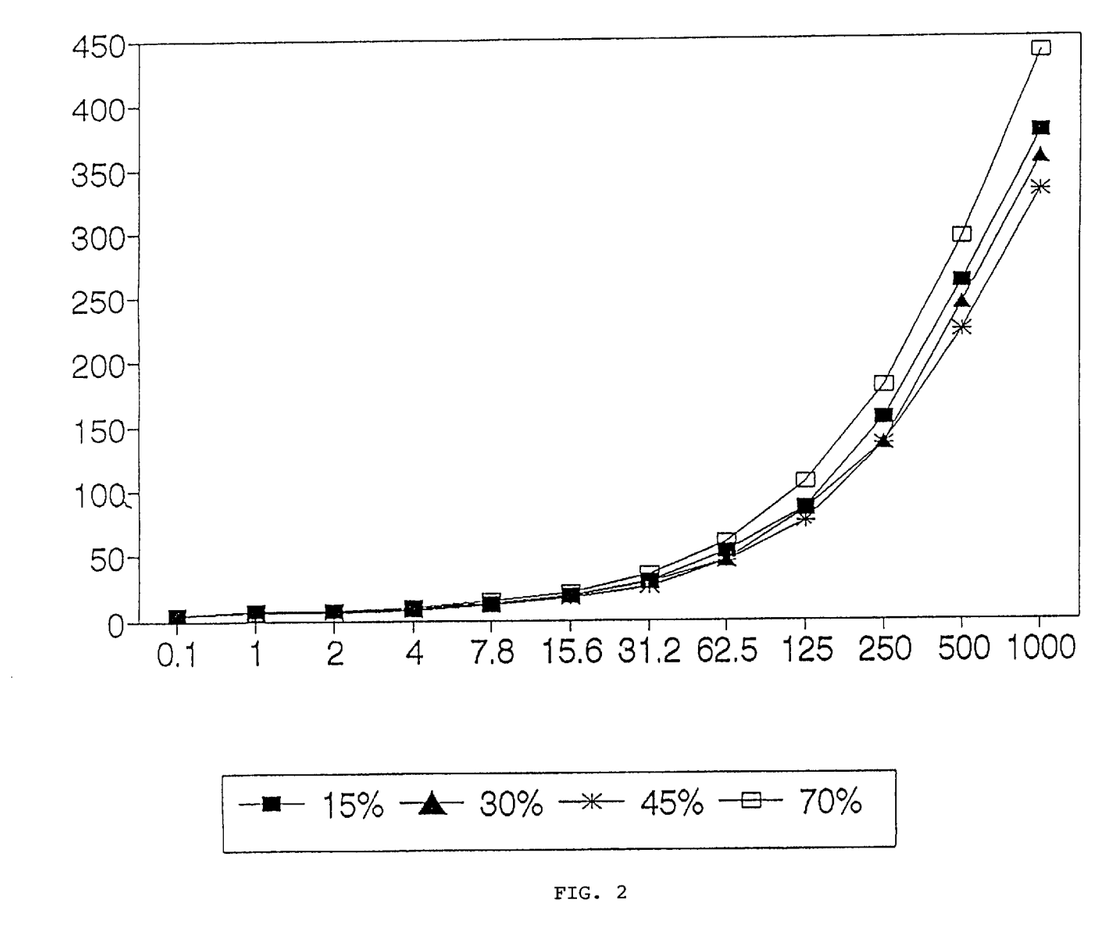
FIG. 2 is a standard curve for Mx antigen in a chemiluminescent immunoassay according to the present invention, derived from solutions in which proteolytic degradation of Mx had been inhibited in accordance with a method of the present invention, in solutions where the hematocrit is 15, 30, 45 and 70% in units of thousands of relative light units (RLU) vs. Mx concentration in units of ng/ml.

FIG. 2 graphically illustrates that, upon dilution of the matrices up to 20-fold with a buffer (e.g., 50 mM Tris-HCl (pH 8.0))containing 2M urea +0.1% SDS, all four matrices which represent hematocrits between 15% and 70% generated similar signal output. The protease inactivation process works best at this dilution as well. Therefore this dilution procedure was incorporated as a part of the standard sample preparation.

B. Effect of detergent concentration on the level of non-specific binding and signal output.

In spite of the 2% (v/v) NP-40 detergent present in the whole blood lysates or synthetic matrices, the final concentration of detergent in the assay mixture was low, as solutions were diluted 20-fold with a media containing 2M urea (denaturing agent) and 0.1% SDS (solubilizing detergent). Therefore, several concentrations of NP-40 (i.e. 0.5, 1 and 2%) were tested in the media containing the detector antibody to determine whether the concentration of detergent (0.2%) would be sufficient to block the non-specific binding of the DMAE-labeled antibody to the solid phase (PMP). We found that concentration of Tergitol NP-40 at 2% (v/v) in the media containing the acridinium ester labeled antibody gave the best signal/noise ratio. Below this level of detergent (0.525% Tergitol NP-40 in the assay mixture), the level of non-specific binding was high, particularly at the lower range of Mx protein concentrations (below approximately 4 ng/ml), while the signal output was lower if the detergent concentration was above this range. We also found that including 50 mM 2-ME in the assay mixture elevated the level of non-specific binding without enhancing the solubility of Mx protein. Therefore, 2-ME included in the original buffer cocktail to enhance the solubility of Mx protins was deleted in our denaturing media, hence in the assay mixture.

C. Effect of incubation time on assay sensitivity level.

Since the level of Mx protein in normal healthy volunteers was at the detection limit of the instant assay, we examined whether the sensitivity limit of the assay could be extended by longer incubation length. As the length of incubation was increased from 30 min. to 2 hours, the absolute signal output was higher. However, it did not extend the sensitivity limit nor improve the precision of the assay at the lower end of Mx antigen concentrations. Therefore, a 30 minute incubation length was chosen.

6. Dilution and recovery of Mx protein.

In order to ensure that the Mx protein assay produced a linear dose-responsive curve in a wide range of Mx protein concentration, Mx protein was serially diluted in the same assay media and assayed at seven different Mx concentrations. The average recovery of Mx protein tested on 3 separate ACS:180 instruments gave an average recovery of 95.9%, with a sensitivity limit of 1 ng/ml, indicating that the assay performance is concentration-independent.

Example 5

Inhibition of Proteolytic Degradation of a Thermally-Stable Protein

A known quantity of recombinant Mx protein was spiked into whole blood lysates or synthetic matrices and incubated at 37° C. Aliquots of samples were taken out periodically and kept on ice until assayed for the residual Mx protein.

Removal of protease activity in the whole blood lysates or synthetic matrices was examined after first diluting the cell lysates or synthetic matrices with various volume ratios of a solution containing a denaturing agent and a solubilizing detergent, specifically 2M urea+0.1 (w/v)% SDS in 50 mM Tris-HCl buffer solution (pH 8.0). The diluted mixtures were then subjected to heat treatment at 56° C. for 30 min. or 90° C. for 60 sec. in a water bath. Effectiveness of heat treatment in destroying the protease activity of the synthetic matrices or whole blood lysates was examined after spiking with a known quantity of Mx protein into the heat-treated media and observing the changes of Mx protein level upon further incubation at 37° C. for up to 120 min.

A buffered solution containing 2M urea+0.1% SDS +50 mM Tris-HCl (pH 8.0) was prepared, followed by heat treatment to investigate the effect on protease activity. Synthetic matrices or whole blood lysates were diluted up to 20 fold (v/v) with the above solution and subjected to heat treatment at 90° C. for 60 sec. or at 56° C. for 30 min. Following the heat treatment, solutions were further incubated at 37° C. for 60 min. and the residual protease activity was assessed with aliquots of samples taken out during this incubation period.

Figure 3:
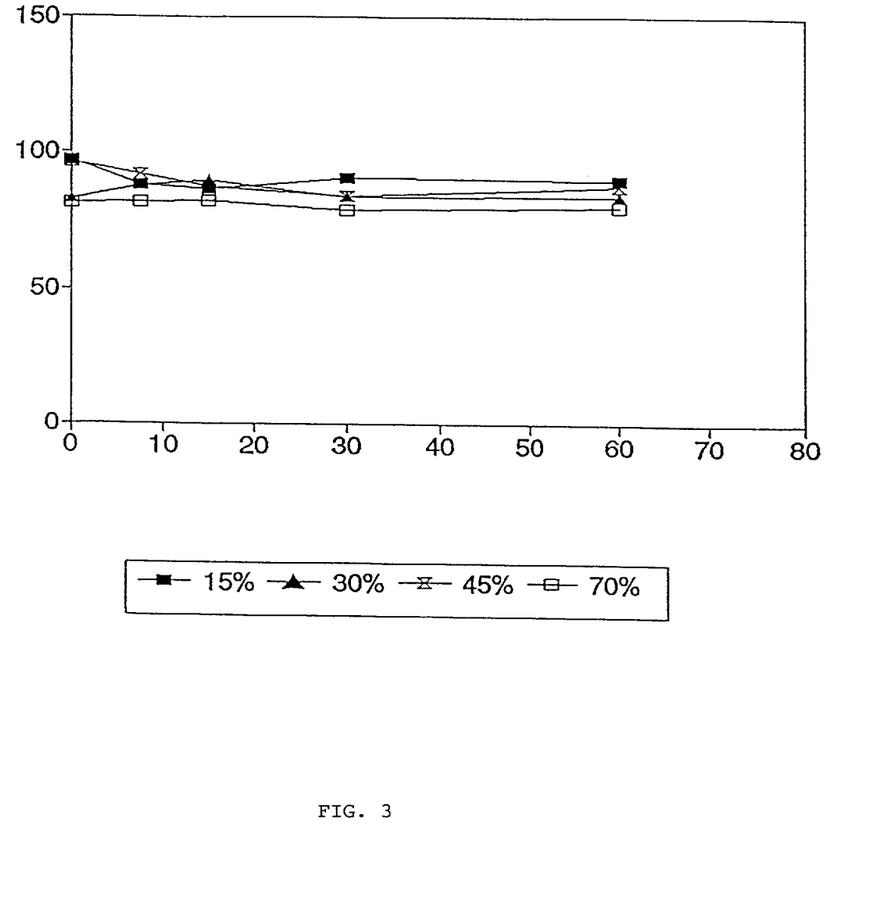
FIG. 3 is a graphic illustration of elimination of proteolytic degradation of Mx protein in synthetic matrices in accordance with the present invention, via heat inactivation after heating in 2M urea and 0.1% SDS, in synthetic matrices having hematocrits of 15, 30, 45 and 70%, in units of thousands of relative light units (RLU) vs. time (in minutes) at 37° C.

As shown in FIG. 3, Mx protein spiked into the 4 different synthetic matrices, which had been heat-inactivated in accordance with the present invention, remained stable for at least 1 hour at 37° C., indicating that the protease activity of the cell lysates was virtually abolished. Essentially identical results were obtained by heating at 90° C. for 60 sec.

Figure 4:
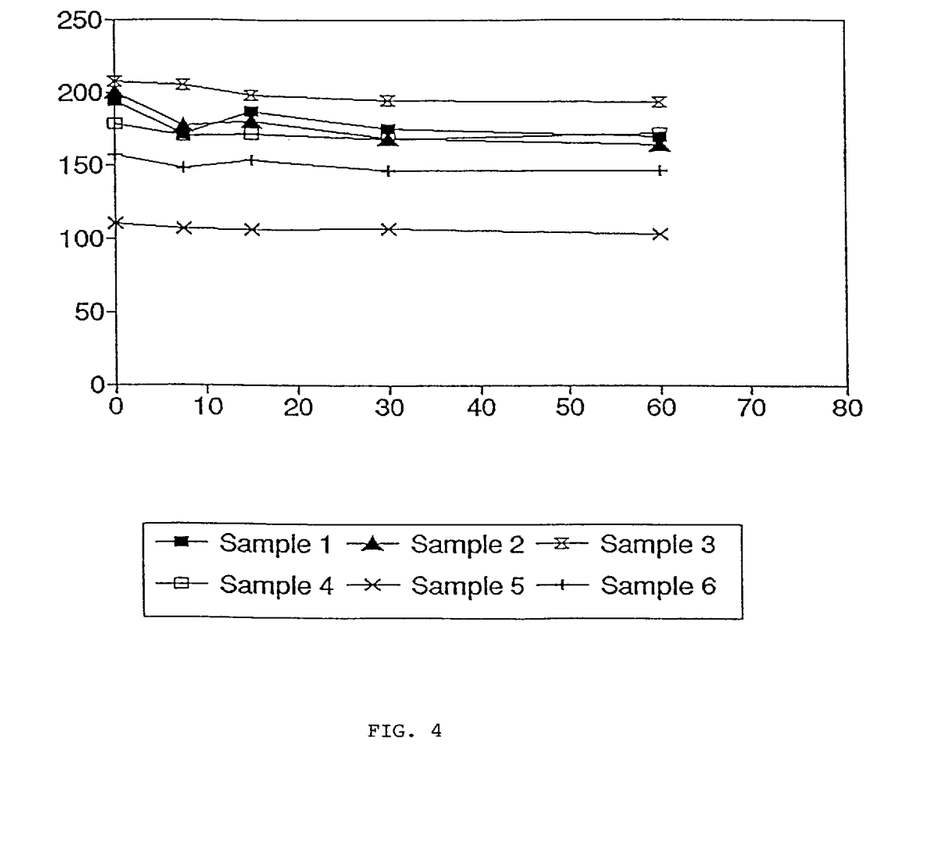
FIG. 4 is a graphic illustration of elimination of proteolytic degradation of Mx protein in whole blood lysates in accordance with the present invention, via heating in urea at 56° C. for 30 minutes, in units of thousands of relative light units (RLU) vs. time (in minutes) at 37° C.

As shown in FIG. 4, Mx protein spiked into 6 different individuals'whole blood lysates also remained stable at least for 1 hour at 37° C. following the heat-inactivation procedure in accordance with the present invention.

The inhibition method of the present invention was also tested with several commercially available proteases. i.e. Cathepsin G and elastase from human leukocytes, and trypsin and elastase type IV from porcine pancreas. It was determined that the method of the present invention is also effective in eliminating the enzymatic activity of the purified proteases up to an equimolar ratio of enzyme (E) to substrate (S).

In order to assess the stability of Mx protein contained in frozen whole blood lysates, a known quantity of purified rMx protein was spiked into 4 different whole blood lysates derived from normal healthy volunteers and stored at 4° C., –20° C. and –80C. Endogenous levels of Mx protein in these whole blood lysates had been previously determined and found to be negliqible. An aliquot of stored sample was taken out every week and immediately diluted with a 20× volume of 2M urea +0.1% SDS in 50 mM Tris HCl buffer (pH 8.0) and heated to 56° C. for 30 min. in order to minimize further degradation of Mx protein during assay procedure. Mx protein kept in whole blood lysates underwent an appreciable degree of autolysis even at –80° C. and more pronounced destruction at 4° C. (25% destruction in 1 week). In contrast, Mx protein kept in heat-treated lysates in accordance with the present invention remained stable both at –80° C. and at 4° C. for at least 3 weeks, further demonstrating the effectiveness of this simple procedure in halting the proteolytic degradation of Mx protein in cell lysates.

Whole blood lysates were prepared with freshly drawn blood from normal healthy volunteers and served as untreated normal controls. Ninety eight samples of frozen whole blood lysates derived from a clinical trial of interferon (B/D) were tested for Mx protein using the manual assay. A total of 26 patients with various types of malignancies had been treated with interferon (B/D) doses from $2\times10^6$ to $64\times10^6$ units/day for days 1,2,3 and 7, or 8 or 9. Groups of three patients were treated with each dose of interferon (B/D) at 2,4,8,16,32,64 and 25 million units per day.

Figure 5:
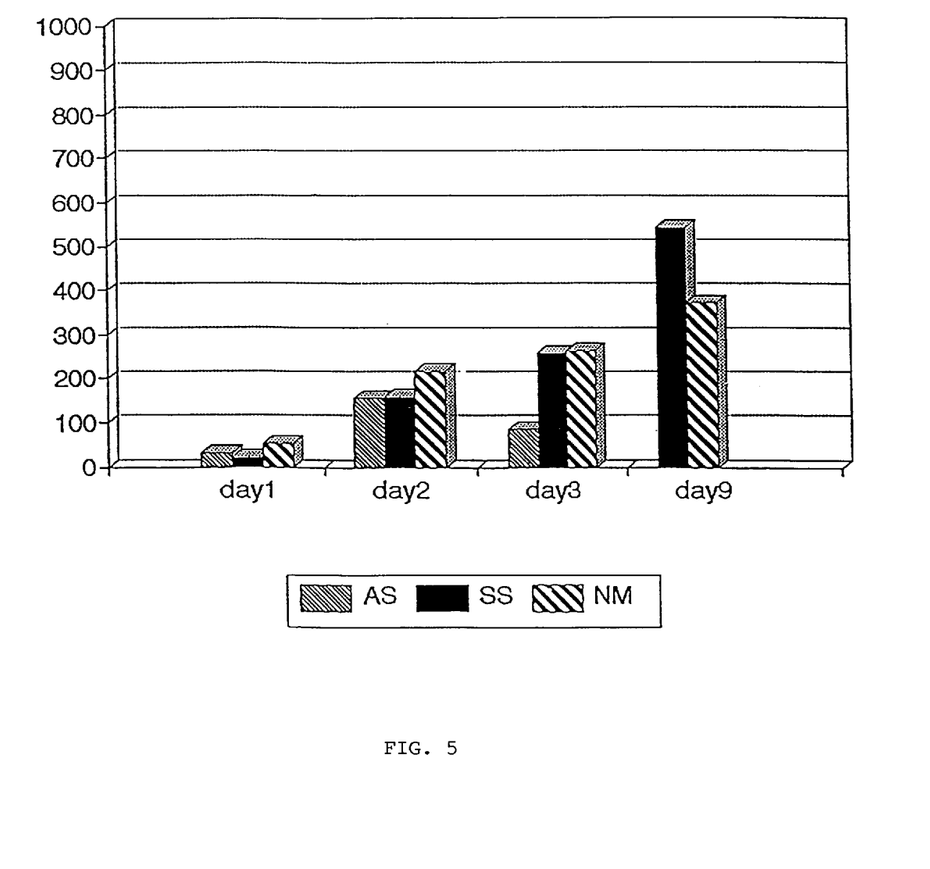
FIG. 5 is a graphic illustration of a typical dose-responsive induction of Mx protein after interferon administration to three human patients, determined in accordance with an assay of the present invention, using $8 \times 10^6$ units/day of IFN (B/D), showing the response on various days in units of Mx concentration (in ng/ml) in whole blood.

FIG. 5 shows a typical dose-dependent Mx induction response for three patients who were treated with IFN (B/D) at $8\times10^6$ units/day. The data was collected according to the method of the invention.

Example 6

Comparison between manual vs. automated assay

The maximum incubation time on our automated assay on the ACS:180 is only 7.5 min., while the length of incubation in the manual assay is adjustable. To compare the manual vs. automated assay performances, we chose to incubate the assay mixture for 30 min. at 37° C. in the manual assay. The results demonstrated that the manual assay values are barely higher than those of the automated assay, considering the longer incubation-time of the manual assay. The two assays exhibited an excellent linear correlation (R=0.987).

Example 7

Comparative Example: Conventional Protease Inhibitors

At least 14 different protease inhibitors listed in the Materials and Methods section including an elastase inhibitor, elastinal, and cysteine-protease inhibitor, E-64, failed to block the protease activity of either the whole blood lysates or the synthetic matrices. In fact, inclusion of these protease inhibitors in whole blood lysate exacerbated proteolytic degradation of Mx protein. Use of a high concentration of chaotropic salts (i.e. 3M sodium thiocyanate, or potassium chloride), denaturing salts such as 8M urea or 6M guanidine-Hcl, or exposure to extreme pHs (pH2 or 11) all failed to arrest the proteolytic degradation of Mx protein.

Those skilled in the art will readily appreciate that all parameters listed herein are meant to be exemplary and actual parameters will depend on the specific application for which the sealing and grounding arrangements are being used. It is, therefore, to be understood that the foregoing embodiments are presented by way of example only and that, within the scope of the appended claims and equivalents thereto, the invention may be practiced otherwise than as specifically described.

What is claimed is:

1. A method of determining the presence of Mx protein contained within the cellular material contained in a sample, said sample also containing protease, comprising:
    a. lysing the cellular material contained within said sample by use of a non-ionic detergent to release said Mx protein,
    b. inactivating the protease contained within said sample by
        1. adding one or more denaturing agents selected from the group consisting of sodium dodecyl sulfate, urea, and guanidine hydrochloride to said sample containing released intracellular protein and protease to form a solution and
        2. heating said solution at a temperature of from about 50° C. to about 60° C. and for a period of time of from about 60 seconds to about 30 minutes to inactivate said protease,
    c. reacting said solution with monoclonal antibody clones 1302.5.32 and 1302.34.16.2.44, and
    d. detecting the binding of said monoclonal antibody clones to said Mx protein wherein binding is indicative of the presence of MX-protein in said sample.

* * * * *